United States Patent
Zardi et al.

(10) Patent No.: US 7,608,735 B2
(45) Date of Patent: Oct. 27, 2009

(54) PROCESS FOR UREA PRODUCTION AND RELATED PLANT

(75) Inventors: Federico Zardi, Breganzona (CH); Paolo Sticchi, Massagno (CH); Paolo Brunengo, Lugano (CH)

(73) Assignee: Urea Casale S.A. (CH)

( * ) Notice: Subject to any disclaimer, the term of this patent is extended or adjusted under 35 U.S.C. 154(b) by 157 days.

(21) Appl. No.: 11/911,461

(22) PCT Filed: Apr. 6, 2006

(86) PCT No.: PCT/EP2006/003121

§ 371 (c)(1),
(2), (4) Date: Oct. 12, 2007

(87) PCT Pub. No.: WO2006/117050

PCT Pub. Date: Nov. 9, 2006

(65) Prior Publication Data

US 2009/0124830 A1    May 14, 2009

(30) Foreign Application Priority Data

May 4, 2005   (EP)   .................................. 05009781

(51) Int. Cl.
*C07C 273/16*   (2006.01)
*C07C 273/04*   (2006.01)

(52) U.S. Cl. .............................. 564/70; 564/63; 564/67; 564/71; 564/72

(58) Field of Classification Search ................... 564/63, 564/67, 70, 71, 72
See application file for complete search history.

(56) References Cited

U.S. PATENT DOCUMENTS 4,864,059 A    9/1989  Fujii
2004/0116743 A1    6/2004  Mennen

FOREIGN PATENT DOCUMENTS

NL    8900152    8/1990

*Primary Examiner*—Peter G O'Sullivan
(74) *Attorney, Agent, or Firm*—Akerman Senterfitt

(57) ABSTRACT

A process for urea production from ammonia and carbon dioxide, in which part of the aqueous solution comprising urea, ammonium carbamate and ammonia obtained in a urea synthesis section is subjected to dissociation in a treatment section operating at a predetermined medium pressure for the recovery of the ammonium carbamate and of the ammonia contained in it, comprises the step of subjecting the urea aqueous solution resulting from the aforementioned dissociation step to decomposition in a low pressure urea recovery section.

7 Claims, 1 Drawing Sheet

PROCESS FOR UREA PRODUCTION AND RELATED PLANT

FIELD OF APPLICATION

In its most general aspect, the present invention concerns a process for urea production from ammonia and carbon dioxide, made to react at a predetermined high pressure in an appropriate synthesis section.

In particular, the invention refers to a process of the aforementioned type in which the product of the ammonia/carbon dioxide reaction, essentially consisting of an aqueous solution comprising urea, ammonium carbamate and ammonia, is subjected to a high-pressure recovery step of the ammonium carbamate and of the ammonia, which are recycled to the synthesis section, whereas the urea aqueous solution is sent to a urea recovery section operating at a predetermined low pressure to obtain urea with the least possible amount of possible residues of ammonia and carbon dioxide.

More specifically, the present invention concerns a process of the type considered, in which the aforementioned recovery of carbamate and ammonia comprises the steps of decomposition of the carbamate and stripping, preferably with a gaseous reactant (in particular $CO_2$), of the ammonia and carbon dioxide thus produced, in a respective stripping zone, subsequent recondensation, in a respective condensation zone, of said ammonia and carbon dioxide into carbamate that is recycled to the synthesis section and in which said steps, together with the urea synthesis reaction, are all carried out substantially at the same high pressure (for example 135-175 bar), constituting a loop called, in the technical field, "High Pressure Loop" or "High Pressure Synthesis Loop" (H.P. Loop).

The invention also refers to a plant for carrying out the aforementioned process.

PRIOR ART

It is well known to produce urea in industrial plants that carry out processes of the type specified above.

There is also a well known requirement to increase the capacity of such plants with respect to the design capacity for which such plants had originally been designed to face up to the ever greater requirement for synthesis urea.

For such a purpose, processes have been proposed in the field that foresee a medium pressure treatment step (10-40 bar) of a part of the aqueous solution comprising urea coming from the synthesis section for the recovery of the ammonium carbamate and ammonia contained in it.

In particular, such a medium pressure treatment section comprises a dissociation step followed by a stripping step with feed $CO_2$ of the aqueous solution comprising urea, ammonium carbamate and ammonia and a subsequent condensation step of the vapours (ammonia, $CO_2$ and water) thus obtained with the addition of feed ammonia and a carbamate aqueous solution (carbonate) coming from the low pressure urea recovery section. The carbamate aqueous solution obtained from the medium pressure condensation step is then recycled to the high pressure synthesis loop (H.P. loop).

A process of this type is for example described in WO-A-02/09323 or else in NL-A-8 900 152.

Whilst they allow the aforementioned requirement to be at least partially satisfied, such processes for urea production of the aforementioned type have recognized drawbacks linked to the need to require the use of additional amounts of condensing water for the condensation of the feed $CO_2$ used as stripping agent in the medium pressure stripping step and of feed ammonia added at the medium pressure condensation step.

This additional use of condensation water is to the detriment of the conversion yield in the urea synthesis section and consequently of the efficiency and of the energy consumption of such a section as well as the efficiency and the energy consumption of the low pressure urea recovery section.

SUMMARY OF THE INVENTION

The technical problem underlying the present invention is that of devising and providing a process for urea production of the type considered above, in which a high production capacity of the plant intended to carry it out can be achieved and at the same time that ensures a high conversion yield of the carbon dioxide to urea in an efficient manner and with low energy consumption, overcoming the aforementioned drawbacks with reference to the prior art.

This problem is solved, according to the present invention, by a process for urea production from ammonia and carbon dioxide, comprising the steps of:

feeding ammonia and carbon dioxide into a urea synthesis section operating at a predetermined high pressure;

making said ammonia and said carbon dioxide react in said synthesis section obtaining an aqueous solution comprising urea, ammonium carbamate and ammonia;

feeding a part of said aqueous solution comprising urea, ammonium carbamate and ammonia to a treatment section operating at a predetermined medium pressure for the recovery of the ammonium carbamate and of the ammonia contained in it;

subjecting said part of aqueous solution comprising urea, ammonium carbamate and ammonia to dissociation in said treatment section obtaining an urea aqueous solution and a vapour phase comprising ammonia, carbon dioxide and water;

subjecting said vapour phase comprising ammonia, carbon dioxide and water to condensation in said treatment section obtaining an ammonium carbamate aqueous solution;

recycling said ammonium carbamate aqueous solution to said urea synthesis section;

characterized in that it comprises the further steps of:

feeding said urea aqueous solution obtained by dissociation in said treatment section to a decomposer of a urea recovery section operating at a predetermined low pressure;

subjecting said urea aqueous solution to decomposition in said decomposer of said urea recovery section obtaining a concentrated urea solution and a second vapour phase comprising ammonia, carbon dioxide and water;

subjecting said second vapour phase to condensation in a condenser of said urea recovery section in fluid communication with said decomposer obtaining a recycle ammonium carbamate aqueous solution.

Preferably, the process according to the present invention also comprises the steps of:

feeding carbon dioxide to said condenser of said urea recovery section;

subjecting said carbon dioxide with said second vapour phase to condensation in said condenser of said urea recovery section obtaining a recycle ammonium carbamate aqueous solution.

In this respect, particularly advantageous results have been achieved by feeding an amount of carbon dioxide comprised between 1 and 10 wt. % of all of the feed carbon dioxide to said condenser of said urea recovery section.

Preferably, said part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

Again preferably, said medium pressure of the treatment section is comprised between 10 and 70 bar.

According to a preferred embodiment of the present invention, said recycle ammonium carbamate aqueous solution obtained in said condenser of the low pressure urea recovery section is fed to said condensation step of the vapour phase comprising ammonia, carbon dioxide and water in said treatment section.

Preferably, said condensation step of the vapour phase comprising ammonia, carbon dioxide and water in said treatment section is of the double-effect type.

Thanks to the process according to the present invention, it has surprisingly and advantageously been found that the amount of condensation water (in absolute value) necessary to recycle the unreacted ammonia and the carbon dioxide in the form of ammonium carbamate to the synthesis section is substantially less with respect to the amount of condensation water (in absolute value) required to carry out such recycling with the processes according to the prior art, in which feed carbon dioxide and feed ammonia are fed to the medium pressure treatment section.

This is due to the fact that, with the same production capacity of the plant for urea production, the amount of ammonia and carbon dioxide to be recycled to the synthesis section in the form of ammonium carbamate is substantially less with the process according to the present invention with respect to with the processes of the prior art.

Resulting from this there is a significant increase in the conversion yield of the urea synthesis section, as well as of the overall yield of the H.P. Loop, to the great advantage of the efficiency and the energy consumption of the plant intended to carry out the process according to the present invention.

In accordance with a further aspect of the present invention, the present technical problem is solved by a plant for carrying out the aforementioned process, comprising a high-pressure urea synthesis section, a medium pressure treatment section of a part of the urea solution produced in said synthesis section, comprising a dissociator and a condenser, and a low pressure urea recovery section comprising a decomposer and a condenser, such sections being in fluid communication with each other, the plant being characterized in that it comprises a connection duct between said dissociator of the medium pressure treatment section and said decomposer of the low pressure urea recovery section.

In accordance with the present invention, the plant for urea production according to the aforementioned process can be a brand new plant or else can be obtained by modifying a pre-existing plant in order to increase its capacity.

In this last case, in accordance with a further aspect of the present invention, a method for revamping a pre-existing plant for urea production from ammonia and carbon dioxide of the type comprising a high-pressure urea synthesis section and a low pressure urea recovery section comprising a decomposer and a condenser, such sections being in fluid communication with each other, is provided which is characterized in that it comprises the steps of:

providing a medium pressure treatment section of a part of the urea solution produced in said synthesis section, comprising a dissociator and a condenser, said medium pressure treatment section being placed in fluid communication with said high pressure urea synthesis section and said low pressure urea recovery section, respectively; and providing a connection duct between said dissociator of the medium pressure treatment section and said decomposer of the low pressure urea recovery section.

Further features and advantages of the process for urea production according to the present invention shall become clearer from the following description of a preferred embodiment thereof, given for indicating and not limiting purposes with reference to the attached drawing.

DETAILED DESCRIPTION OF A PREFERRED EMBODIMENT

Figure 1:
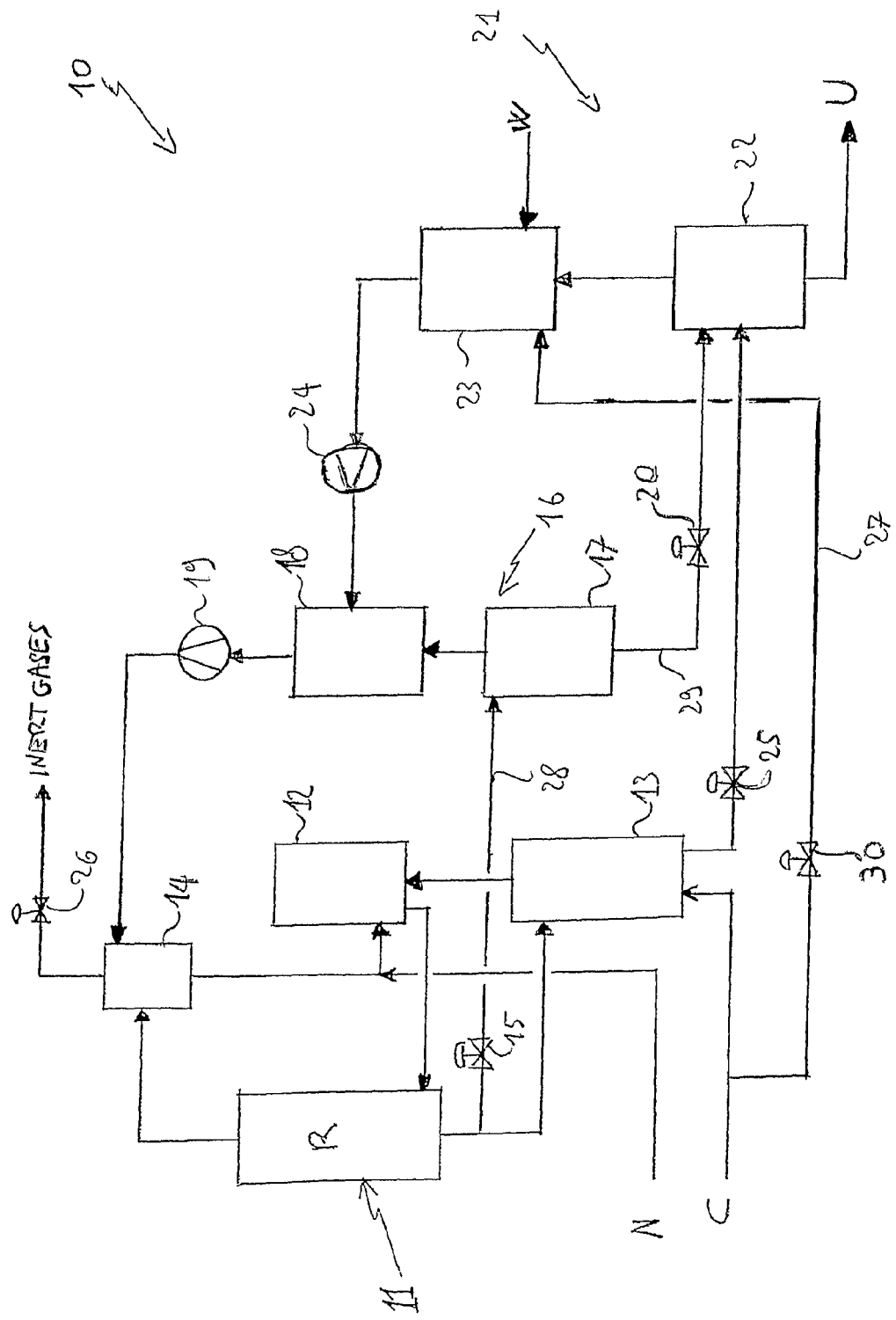
FIG. 1 schematically represents a plant for urea production that carries out the process of the present invention.

With reference to FIG. 1, a plant, wholly indicated with 10, for urea production is shown, which carries out the process according to the present invention.

According to the aforementioned process for urea production, ammonia N and carbon dioxide C are fed into an appropriate synthesis section 11. In the example of FIG. 1, the urea synthesis section comprises a single reactor R.

In particular, according to such an example, the ammonia N is fed to the reactor R through a condenser 12 and the carbon dioxide C is in turn fed to the reactor R through a stripper 13 and the condenser 12.

The synthesis section 11 (reactor R), the condenser 12, the stripper 13, together with a scrubber 14 (that shall be described hereafter in greater detail), all operate substantially at the same high pressure, thus constituting the high pressure synthesis loop (H.P. Loop) of the process of the present invention.

In the reactor R, or rather in the synthesis section 11, the ammonia and carbon dioxide are made to react at the aforementioned predetermined high pressure (for example comprised between 130 and 170 bar) and at a predetermined high temperature (for example comprised between 160 and 200° C.). From the reactor R an aqueous solution comprising urea, ammonium carbamate and ammonia is obtained.

A part of the aqueous solution comprising urea, ammonium carbamate and ammonia exiting the reactor R is suitably decompressed in a per se conventional way for example by means of a valve 15 and fed to a treatment section 16 of such an aqueous solution operating at a predetermined medium pressure, for example comprised between 10 and 70 bar, preferably comprised between 15 and 25 bar, and even, more preferably comprised between 18-20 bar.

For the recovery of the ammonium carbamate and the ammonia, the part of aqueous solution comprising urea, ammonium carbamate and ammonia suitably decompressed is fed to a medium pressure dissociator 17 at the treatment section 16 and subjected to dissociation obtaining an urea aqueous solution and a vapour phase comprising ammonia, carbon dioxide and water. In particular, such a part of aqueous solution comprising urea, ammonium carbamate and ammonia is subjected in the dissociator 17 to thermal dissociation.

The vapour phase comprising ammonia, carbon dioxide and water thus obtained is then fed and subjected to condensation in a medium pressure condenser 18 of the treatment section 16. In the condenser 18 an ammonium carbamate aqueous solution is obtained that exits the condenser 18 and is recycled to the urea synthesis section 11 (reactor R).

In the example of FIG. 1, the carbamate aqueous solution exiting the medium pressure condenser 18 is suitably compressed in a per se conventional way for example by means of a pump 19 and recycled to the reactor R of the high pressure urea synthesis section 11 through the scrubber 14 and the high pressure condenser 12. According to an alternative embodiment of the present invention, not represented, at least a part of the carbamate aqueous solution exiting the medium pressure condenser 18 is fed, suitably compressed, directly to the high pressure condenser 12 to then flow into the reactor R.

In accordance with the present invention, the process for urea production advantageously foresees the further step of feeding the urea aqueous solution obtained by dissociation in the medium pressure dissociator 17 of the treatment section 16 to a decomposer 22 of a urea recovery section 21 operating at a predetermined low pressure, for example comprised between 1.5 and 9.5 bar, preferably comprised between 3 and 5 bar.

For this purpose, the urea aqueous solution exiting the dissociator 17 is suitably decompressed in a per se conventional way for example by means of a valve 20.

In particular, as represented in the preferred embodiment of the process according to the present invention of FIG. 1, the urea aqueous solution exiting the dissociator 17 of the treatment section 16 is directly fed to the decomposer 22 of the urea recovery section 21.

Moreover, again in accordance with the example of FIG. 1, a part of the feed carbon dioxide C is preferably and advantageously fed to a condenser 23 of the low pressure urea recovery section 21.

For this purpose, such a part of feed carbon dioxide C sent to the condenser 23 is suitably decompressed in a per se conventional way for example by means of a valve 30.

In the decomposer 22 of the low pressure urea recovery section 21, the urea aqueous solution coming from the dissociator 17 of the medium pressure treatment section 16 is subjected to decomposition obtaining a concentrated urea solution U and a second vapour phase comprising ammonia, carbon dioxide and water.

The concentrated urea solution U, for example with a urea concentration comprised between 60 and 80 wt. %, exits the decomposer 22 of the urea recovery section 21 to be subjected to the final urea treatment steps (per se conventional and therefore not represented) of the process for urea production, such as the vacuum decomposition step and the granulation or prilling step of the molten urea thus obtained.

In accordance with the process according to the present invention, the second vapour phase comprising ammonia, carbon dioxide and water obtained in the decomposer 22 of the urea recovery section 21 is, on the other hand, sent to the condenser 23 of the same section 21 and advantageously subjected to condensation obtaining a recycle carbamate aqueous solution.

Preferably, as represented in the example of FIG. 1, the second vapour phase comprising ammonia, carbon dioxide and water is subjected to condensation together with the feed carbon dioxide C fed to said condenser 23.

A suitable amount of an carbamate aqueous solution (carbonate) having a condensation water content comprised between 40 and 80 wt. % is also fed to the condenser 23 of the low pressure urea recovery section 21, to allow the second vapour phase and the feed carbon dioxide C, respectively, to condense to ammonium carbamate.

The carbamate aqueous solution W (carbonate) generally comes from a treatment section of the process condensate and/or from an ammonia liquor reservoir, per se conventional and not represented in FIG. 1.

Preferably, as represented in the example of FIG. 1, the recycle carbamate aqueous solution obtained in the condenser 23 of the low pressure urea recovery section 21 is, according to the present process, fed into the medium pressure condenser 18 of the treatment section 16 for the absorption (condensation) of the vapour phase comprising ammonia, carbon dioxide and water coming from the medium pressure dissociator 17.

In this case, the step of compressing the recycle carbamate aqueous solution exiting the condenser 23, to the operating pressure of the treatment section 16 is also foreseen in a per se conventional way for example by means of a pump 24.

According to an alternative embodiment of the process according to the present invention, not represented, the condensation step in the condenser 18 of the medium pressure treatment section 16 is of the double effect type, in which the condensation heat, instead of being dissipated in a cooling fluid (generally cooling water), is advantageously exploited to further concentrate the concentrated urea solution U exiting the decomposer 22 of the low pressure urea recovery section.

In this case, the condensation heat that develops during the condensation of the vapour phase is transmitted by indirect heat exchange to the concentrated urea solution U, allowing the decomposition and therefore the separation of a part of the ammonium carbamate, ammonia and water still present in such a solution and thus further concentrating the urea contained in it.

The remaining part of aqueous solution comprising urea, ammonium carbamate and ammonia, exiting the reactor R and not sent to the medium pressure treatment section 16, is subjected to the recovery phase of the ammonium carbamate and of the ammonia present in such a solution, in the high pressure loop of the present process.

In particular, the remaining part of the aqueous solution comprising urea, ammonium carbamate and ammonia exiting the reactor, R of the synthesis section 11 is fed to the high pressure stripper where it is subjected to decomposition and stripping with feed carbon dioxide C. The ammonia and carbon dioxide thus produced are then recondensed into ammonium carbamate in the high pressure condenser 12 and recycled in the form of ammonium carbamate to the reactor R of the urea synthesis section 11.

The condensation in the high pressure condenser 12 of the ammonia and carbon dioxide coming from the stripper 13 is made to occur by absorption of such gases with the feed ammonia N (liquid) and with the carbamate aqueous solution coming, suitably compressed, from the condenser 18 of the medium pressure treatment section 16, through the scrubber 14.

The aqueous solution comprising urea, ammonium carbamate and ammonia obtained in the stripper 13 following the aforementioned decomposition and stripping steps with $CO_2$ is suitably decompressed in a per se conventional way for example by means of a valve 25 at the operating pressure of the urea recovery section 21 and fed to the low pressure decomposer 22 of such a section 21. Here, such a solution is subjected to decomposition, together with said urea aqueous solution coming from the dissociator 17 of the medium pressure treatment section 16, obtaining the concentrated urea solution U and the second vapour phase comprising ammonia, carbon dioxide and water, described above.

The unreacted carbon dioxide and ammonia and water in vapour phase present in the urea synthesis section 11, or rather in the reactor R, are made to exit the latter and fed to the high pressure scrubber 14. These vapours generally also comprise inert gases (for example air) present in the feed carbon dioxide C.

In the scrubber 14, the aforementioned vapours are subjected to a washing treatment with the carbamate aqueous solution coming, suitably compressed, from the condenser 18 of the medium pressure treatment section 16, for the recovery of the carbon dioxide and ammonia present in them and the separation of the inert gases. The inert gases thus separated are then released into the atmosphere in a per se conventional manner, moreover foreseeing suitable decompression thereof for example by means of a valve 26. Alternatively, such inert gases can be recycled in other parts of the plant (not represented). The carbon dioxide and ammonia absorbed in the carbamate aqueous solution coming from the condenser 18 are, on the other hand, recycled to the urea synthesis section 11, or rather to the reactor R, through the high pressure condenser 12.

With the process according to the present invention, particularly advantageous results have been obtained by feeding an amount of feed carbon dioxide C comprised between 1 and 5 wt. %, even more preferably comprised between 2 and 3 wt. %, of all of the feed carbon dioxide C fed to the plant 10, to the condenser 23 of the low pressure urea recovery section 21.

Moreover, the part of aqueous solution comprising urea, ammonium carbamate and ammonia sent to the medium pressure treatment section 16 is preferably comprised between 10 and 50 wt. %, even more preferably comprised between 10 and 25 wt. %, of the aqueous solution coming from the urea synthesis section 11.

With reference to FIG. 1, the structural features of the plant 10 for synthesis urea production from ammonia and carbon dioxide according to the process of the present invention just described shall now be better specified.

In accordance with the present invention, the plant 10 comprises a high pressure urea synthesis section 11, a medium pressure treatment section 16 and a low pressure urea recovery section 21 arranged in fluid communication with each other.

The treatment section 16 advantageously comprises a medium pressure dissociator 17 and a medium pressure condenser 18 in fluid communication with each other. In turn, the urea recovery section 21 comprises a low pressure decomposer 22 and a low pressure condenser 23 in fluid communication with each other.

In the plant 10 respective feed ducts are foreseen of the reactants, carbon dioxide C and ammonia N, and of an carbamate aqueous solution W (carbonate) comprising condensation water, as well as connection ducts between the different sections and the corresponding apparatuses, schematically represented in FIG. 1 by the different flow lines.

In particular, in the plant 10 connection ducts 28 and 29 are advantageously foreseen for the direct connection between the urea synthesis section 11 and the dissociator 17 of the medium pressure treatment section 16, and between this apparatus and the decomposer 22 of the low pressure urea recovery section 21, respectively.

Moreover, according to the preferred embodiment of the present invention represented in FIG. 1, a duct 27 for feeding feed carbon dioxide C to the condenser 23 of the low pressure urea recovery section 21 is also foreseen.

According to an alternative embodiment, not represented, of the plant 10 according to the present invention, the medium pressure condenser 18 comprises a conventional tube bundle, in fluid communication, on the inside, i.e. tube side, with the concentrated urea solution U exiting the low pressure decomposer 22, and in fluid communication; on the outside, i.e. shell side, with the vapour phase comprising ammonia, carbon dioxide and water coming from the medium pressure dissociator 17 as well as with the recycle carbamate aqueous solution coming from the low pressure condenser, to obtain the double effect described above.

From the previous description it can clearly be seen that the process for urea production according to the invention solves the technical problem and achieves numerous advantages the first of which lies in the fact that a high overall conversion yield is obtained in the high pressure loop, and in particular in the urea synthesis section, for example comprised between 58 and 62 wt. %, irrespective of the required production capacity of the plant provided to carry it out.

The claimed process is thus also particularly advantageous for high capacity plants, for example to produce between 3000 and 4500 Metric Ton/day of urea.

A further advantage is that, thanks to the present invention and in particular to the high conversion yield, it is possible to reduce the energy consumption of the high pressure synthesis loop as well as of the low pressure urea recovery section, with respect to the processes according to the prior art. It follows from this that with the same energy consumption and size of the apparatuses that constitute the plant for urea production, the process according to the present invention allows operation in such a plant with a higher production capacity with respect to what is allowed with the processes according to the prior art. In other words, with the same production capacity, the plant intended to carry out the process according to the present invention is smaller in size, and thus more cost-effective and with less operating costs, with respect to the plant necessary to obtain such a capacity with the methods of the prior art.

Moreover, the actuation of the process is particularly simple and reliable, and does not require large investment costs.

The aforementioned advantages are mainly linked to the fact that thanks to the studies carried out by the Applicant it has surprisingly been found that by subjecting the urea aqueous solution obtained by dissociation in the medium pressure treatment section 16 to low pressure decomposition, the amount (in absolute value) of condensation water contained in the carbamate aqueous solution W (carbonate) required for such condensation to ammonium carbamate is substantially less than the amount of condensation water necessary with the methods according to the prior art.

Given that such condensation water is recycled to the urea synthesis section together with the ammonium carbamate and given that water is a reaction product in urea synthesis and that therefore has a negative influence upon the conversion of the reactants, the fact of managing to substantially reduce such an amount of condensation water has advantageously involved a corresponding increase in the conversion yield with respect to the processes according to the prior art.

In particular, unlike the present invention, the processes according to the prior art necessarily foresee, in the medium pressure treatment section 16, a stripping step with feed carbon dioxide of the urea aqueous solution previously obtained by thermal dissociation in such a section and a condensation step with the addition of feed ammonia. In order to be able to efficiently and totally condense such amounts of feed carbon dioxide and ammonia introduced into the medium pressure treatment section to ammonium carbamate, it is thus necessary to feed a substantially larger amount (in absolute value)

of condensation water to the low pressure urea recovery section than that required with the process according to the present invention.

As an example, it has advantageously been noted that, with the same operating conditions, the aforementioned amount of condensation water contained in the carbamate aqueous solution W (carbonate) is 10-25 wt. % less with the process according to the present invention with respect to the prior art, with a corresponding increase in the conversion yield in the high pressure urea synthesis section of 2-3%.

Amongst the numerous advantages achieved by the present invention it is important to quote the possibility of increasing the production capacity of pre-existing plants for urea production from ammonia and carbon dioxide, with respect to the design capacity for which such plants had originally been designed, in a simple, effective and reliable way and without for this reason having to negatively influence upon the overall conversion yield, the operating costs and the energy consumption of the pre-existing plant. Advantageously, this is also possible for substantial increases in capacity, for example of 30-50%, with respect to the design capacity of the pre-existing plant.

In accordance with the preferred embodiment of the present invention represented in FIG. 1, the plant 10 for urea production is obtained from a revamping method (modernization) of a pre-existing plant for urea production from ammonia and carbon dioxide of the type comprising a high pressure urea synthesis section 11 and a low pressure urea recovery section 21 comprising a decomposer 22 and a condenser 23, such sections 11, 21 being arranged in fluid communication with each other, characterized in that it comprises the steps of:

providing a medium pressure treatment section 16 of a part of the urea solution produced in said synthesis section 11, comprising a dissociator 17 and a condenser 18, said medium pressure treatment section 16 being placed in fluid communication with said high pressure urea synthesis section and said low pressure urea recovery section 11, 21, respectively;

providing a direct connection duct 29 between said dissociator 17 of the medium pressure treatment section 16 and said decomposer 22 of the low pressure urea recovery section 21.

Preferably, the method according to the present invention foresees the further step of providing a duct 27 for feeding feed carbon dioxide C to said condenser 23 of the low pressure urea recovery section 21.

Of course, a man skilled in the art can bring numerous modifications and variants to the process for urea production described above in order to satisfy contingent and specific requirements, all of which are in any case covered by the scope of protection of the present invention, as defined by the following claims.

The invention claimed is:

1. Process for urea production from ammonia and carbon dioxide, comprising the steps of:
   feeding ammonia and carbon dioxide into a urea synthesis section operating at a predetermined high pressure;
   making said ammonia and said carbon dioxide react in said synthesis section obtaining an aqueous solution comprising urea, ammonium carbamate and ammonia;
   feeding a part of said aqueous solution comprising urea, ammonium carbamate and ammonia to a treatment section operating at a predetermined medium pressure for the recovery of the ammonium carbamate and of the ammonia contained in it;
   subjecting said part of aqueous solution comprising urea, ammonium carbamate and ammonia to dissociation in said treatment section obtaining an urea aqueous solution and a vapour phase comprising ammonia, carbon dioxide and water;
   subjecting said vapour phase comprising ammonia, carbon dioxide and water to condensation in said treatment section obtaining an ammonium carbamate aqueous solution;
   recycling said ammonium carbamate aqueous solution to said urea synthesis section;
   characterized in that it comprises the further steps of:
   feeding said urea aqueous solution obtained by dissociation in said treatment section to a decomposer of a urea recovery section operating at a predetermined low pressure;
   subjecting said urea aqueous solution to decomposition in said decomposer of said urea recovery section obtaining a concentrated urea solution and a second vapour phase comprising ammonia, carbon dioxide and water;
   subjecting said second vapour phase to condensation in a condenser of said urea recovery section in fluid communication with said decomposer obtaining a recycle ammonium carbamate aqueous solution.

2. Process according to claim 1, characterized in that it comprises the further steps of:
   feeding carbon dioxide to said condenser of said urea recovery section;
   subjecting said carbon dioxide with said second vapour phase to condensation in said condenser of said urea recovery section obtaining a recycle ammonium carbamate aqueous solution.

3. Process according to claim 2, characterized in that an amount of carbon dioxide comprised between 1 and 10 wt. % of all of the feed carbon dioxide is fed to said condenser of said urea recovery section.

4. Process according to claim 1, characterized in that said part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

5. Process according to claim 1, characterized in that said medium pressure of the treatment section is comprised between 10 and 70 bar.

6. Process according to claim 1, characterized in that said recycle ammonium carbamate aqueous solution obtained in said condenser of the low pressure urea recovery section is fed to said condensation step of the vapour phase comprising ammonia, carbon dioxide and water in said treatment section.

7. Process according to claim 1, characterized in that said condensation step of the vapour phase comprising ammonia carbon dioxide and water in said treatment section is of the double effect type.

* * * * *